United States Patent
Hachtel et al.

(10) Patent No.: US 6,894,184 B2
(45) Date of Patent: May 17, 2005

(54) PROCESS FOR PREPARING 2-CYANO-3-HYDROXY-N-(PHENYL)BUT-2-ENAMIDES

(75) Inventors: Jochen Hachtel, Frankfurt (DE); Bernd Neises, Offenburg (DE); Wilfried Schwab, Neuried (DE); Roland Utz, Messel (DE); Martin Zahn, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 40 days.

(21) Appl. No.: 10/802,583

(22) Filed: Mar. 17, 2004

(65) Prior Publication Data

US 2004/0186173 A1 Sep. 23, 2004

Related U.S. Application Data

(60) Provisional application No. 60/490,329, filed on Jul. 25, 2003.

(30) Foreign Application Priority Data

Mar. 18, 2003 (DE) .......................... 103 11 763

(51) Int. Cl.[7] ............................................. C07C 255/07
(52) U.S. Cl. ........................................ 558/357
(58) Field of Search ........................................ 558/357

(56) References Cited

U.S. PATENT DOCUMENTS

| 3,503,986 A | 3/1970 | Seidel et al. |
| 5,519,042 A | 5/1996 | Morris et al. |
| 5,679,709 A | 10/1997 | Bartlett et al. |
| 5,700,822 A | 12/1997 | Hirth et al. |
| 6,121,316 A | 9/2000 | Schwab et al. |

FOREIGN PATENT DOCUMENTS

EP 0257882 A 3/1988

OTHER PUBLICATIONS

Ghosh, et al., Three leflunomide metabolite analogs, Acta Crystallogr. Sect. C Cryst. Struct. Commun.; 56:10; 2000; pp. 1254–1257.

Veb Deutscher, Umsetzung von Carbonsaurechloriden und −anhydriden, Organikum; 12 Auflage; 1973; p. 525.

*Primary Examiner*—Kamal Saeed
(74) *Attorney, Agent, or Firm*—Ronald G. Ort

(57) ABSTRACT

A process is described for producing 2-cyano-3-hydroxy-N-(phenyl)but-2-enamide, in which a phenyl-substituted 2-cyano-N-(phenyl)acetamide is reacted in the presence of a base, acetic anhydride and at least one solvent, and the resultant 2-cyano-3-hydroxy-N-(phenyl-derivative)but-2-enamide is crystallized by acidification.

9 Claims, No Drawings

PROCESS FOR PREPARING 2-CYANO-3-HYDROXY-N-(PHENYL)BUT-2-ENAMIDES

CROSS-REFERENCE TO RELATED APPLICATIONS

This application claims the benefit of U.S. Provisional Application No. 60/490,329, filed Jul. 25, 2003, and incorporated herein by reference.

DESCRIPTION OF THE INVENTION

The invention relates to a process for preparing 2-cyano-3-hydroxy-N-(phenyl)but-2-enamides from 2-cyano-N-(phenyl)acetamide, in particular the preparation of 2-cyano-3-hydroxy-N-[(4-trifluoromethyl)phenyl]but-2-enamide from 2-cyano-N-(4-trifluoromethylphenyl)acetamide.

The compound 2-cyano-3-hydroxy-N-[(4-trifluoromethyl)phenyl]but-2-enamide is known (U.S. Pat. No. 5,679,709). Processes for preparing 2-cyano-3-hydroxy-N-[(4-trifluoromethyl)phenyl]but-2-enamide are described, for example, in U.S. Pat. Nos. 5,519,042 or 5,700,822. Disadvantages of the known processes are a low yield and a low purity.

It has now been found that 2-cyano-3-hydroxy-N-[phenyl]but-2-enamides can be prepared from 2-cyano-N-(phenyl)acetamide in the presence of acetic anhydride and sodium hydroxide.

The invention therefore relates to a process for producing the compound of formula I

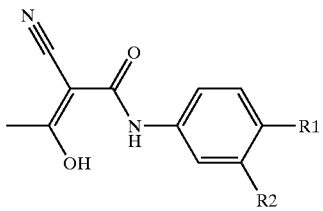

(I)

where

R1 is a) —CF$_3$,
 b) —O—CF$_3$,
 c) —S—CF$_3$,
 d) —OH,
 e) —NO$_2$,
 f) halogen,
 g) benzyl
 h) phenyl,
 i) —O-phenyl,
 k) —CN,
 l) —O-phenyl, monosubstituted or polysubstituted with
  1) —(C$_1$–C$_4$)-alkyl,
  2) halogen,
  3) —O—CF$_3$ or
  4) —O—CH$_3$, and
R2 is
 a) —(C$_1$–C$_4$)-alkyl,
 b) halogen or
 c) a hydrogen atom, which comprises reacting a compound of the formula II,

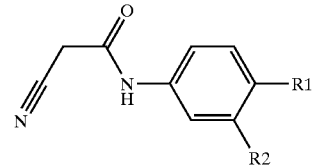

(II)

where R1 and R2 are as defined above, in the presence of at least one base, acetic anhydride and at least one solvent and then isolating the resulting compound of the formula I.

The invention further relates to a process for producing the compound of the formula III

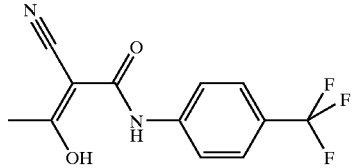

(III)

wherein a compound of the formula IV

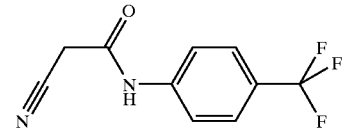

(IV)

is reacted in the presence of water, sodium hydroxide, acetic anhydride and an additional solvent and then the resultant compound of the formula III is isolated.

In the preparation of the compound of the formula I, a procedure is followed in such a manner that, first, the compound of the formula II or (2-cyano-N-(4-trifluoromethylphenyl)acetamide) is placed in a solvent and the resultant solution or suspension is cooled. Aqueous sodium hydroxide and acetic anhydride are then added, and the resultant reaction mixture is then stirred or shaken with cooling.

After an appropriate reaction time, the compound of the formula I is precipitated out using an acid. The compound of the formula I is isolated, for example, by crystallization or extraction, for example using ethyl acetate or toluene. Crystallization is promoted by cooling the suspension or further evaporation of the solvents.

The term "solvents" is taken to mean, for example, water, organic solvents for example:

ketone solvents, such as acetone, methyl ethyl ketone or methyl isobutyl ketone;
halogenated hydrocarbons such as dichloromethane;
alcohols such as ethanol, isopropanol or n-butanol;
ethers such as diisopropyl ether, diethoxymethane, or diethylene glycol dimethyl ether,
hydrocarbons such as toluene;
esters such as ethyl acetate;
aprotic solvents such as dimethylformamide, dimethylacetamide, dimethyl sulfoxide or N-methylpyrrolidone or mixtures of said solvents, or phase-transfer catalysts such as quaternary ammonium or phosphonium salts, for example dimethylditetradecylammonium bromide, benzyltriethylammonium chloride, Alliquat® 336 (3-methyltrioctlylammonium chloride), tetrabutylammonium hydrogen sulfate, or tetrabutylphosphonium chloride;

crown ethers or cryptands such as 18-crown-6 or cryptand 222 [=4,7,13,16,21,24-hexaoxa-1,10-diazabicyclo-(8.8.8) hexacosane], or polyethylene glycols can be used, which is particularly advantageous in the case of slightly water-miscible solvents such as toluene.

The term "bases" is taken to mean alkali metal hydroxides, for example sodium hydroxide or potassium hydroxide, caustic soda in solid form or in the form of lyes of differing concentrations, alkali metal hydrides and alkaline earth metal hydrides, for example sodium hydride, calcium hydride; amides, for example sodium amide; alkoxides, eg sodium methoxide, potassium tert-butoxide, organometallic compounds, for example n-butyllithium; or amines, for example diethylisopropylamine or mixtures of said organic bases. The water present in the lye is then included in the calculation in preparation of the reaction mixture. The term "halogen" is taken to mean fluorine, chlorine, bromine and iodine. The term "—($C_1$–$C_4$)-alkyl" is taken to mean hydrocarbon radicals such as methyl, ethyl, propyl, n-butyl or isobutyl.

Suitable acids are, for example, hydrochloric acid, sulfuric acid, nitric acid or phosphoric acid, or mixtures of the acids.

Preferably, for the inventive reaction, 150 mol to 300 mol of acetic anhydride and 100 mol to 550 mol of sodium hydroxide are used per 100 mol of the compound of the formula II or IV.

The amount of solvent used is generally from 3 kg to 11 kg per kg of the compound of the formulae II or IV, preferably from 4 kg to 6 kg.

The reaction time is generally between a few minutes and 24 hours, preferably 1 to 3 hours, depending on composition of the mixture and the temperature range selected.

The reaction temperature is from −5° C. to 50° C., preferably from 0° C. to 30° C., in particular 10° C.

The residual content of starting substrate of the compound of the formula II or 2-cyano-N-(4-trifluoromethylphenyl) acetamide was reduced below a content of 0.5% in the isolated 2-cyano-3-hydroxy-N-[(4-trifluoromethyl)phenyl] but-2-enamide.

The starting substance for the inventive reaction can be prepared according to methods known from the literature, for example DE 1 900 947.

The process product is biologically active and is suitable, for example, for treating rheumatoid arthritis or multiple sclerosis.

Advantageous features in the inventive process are the very short reaction times, the omission of additional purification steps, the high yields and the high purity of the product prepared. Advantages of the inventive process are the essentially complete reaction to give the compound of the formula I or 2-cyano-3-hydroxy-N-[(4-trifluoromethyl) phenyl]but-2-enamide and a total byproduct content of less than 1%.

EXAMPLE 1

Preparation of 2-cyano-3-hydroxy-N-[(4-trifluoromethyl) phenyl]but-2-enamide 2.5 g of 2-cyano-N-(4-trifluoromethylphenyl)acetamide and 0.127 g of dimethylditetradecylammonium bromide were weighed into a Teflon reactor equipped with a frit. The reactor was blanketed with argon and charged with 15 ml of diethoxymethane. The shaking was turned on and the contents were cooled to 15° C. 1.73 ml of aqueous 50% strength NaOH were added manually and, in the course of 5 to 20 min, a total of 2.12 ml of acetic anhydride were added. Then the reaction mixture was monitored by HPLC repeatedly. The suspension was shaken for a further 8.5 hours (h) after addition of acetic anhydride.

Thereafter, the reactor was cooled to 5° C. In the course of 10 (minutes) min, 3.20 ml of water and 2.90 ml of HCl, 37% were each added, the reactor internal temperature being kept at 5° C. At this temperature the contents were shaken for 1 h. Subsequently, 13.0 ml of water were added to each reactor, warmed to 10° C. and shaken for 1 h. The white suspension was ejected with argon. The remaining solids were washed three times each time with 15.0 ml of water, dried at 45° C. and 150 mbar to constant weight, weighed and analyzed by HPLC.

HPLC Method for 2-cyano-3-hydroxy-N-[(4-trifluoromethyl)phenyl]but-2-enamide

| Test technique: | Liquid chromatography (European Pharmacopoeia) |
|---|---|
| Apparatus: | Liquid chromatograph: Waters Alliance Separations Module 2690 |
| Column: | Material: stainless steel Length: 100 mm Internal diameter: 4.6 mm |
| Stationary phase: | Waters Symmetry-C18 Particle size 3.5 µm |
| Mobile phase: | Acetonitrile: 350 ml Water: 650 ml Triethylamine: 5 ml adjust to pH 6.0 using $H_3PO_4$ 85% |
| Injection volume: | 10 µl |
| Sample applicator temperature: | 12° C. |
| Column temperature: | 20° C. |
| Flow rate: | 0.8 ml/min |
| Run time: | 45 min |
| Detection: | UV/Vis, 210 nm |
| Standard solution: | 14.0 mg of reference standard are sonicated in 2 ml of acetonitrile and made up to 20 ml. |
| Test solution: | 12.5 mg of substance are dissolved with acetonitrile R to give 25 ml. |

| Retention times (min): | absolute | relative |
|---|---|---|
| 2-Cyano-3-hydroxy-N-[(4-trifluoromethyl)-phenyl]but-2-enamide: | 6.4 ± 10% | 1.0 |
| 2-Cyano-N-(4-trifluoromethylphenyl)-acetamide: | 12.8 ± 10% | 2.0 ± 10% |
| 4-Trifluoromethylaniline: | 14.1 ± 10% | 2.2 ± 10% |

$$\text{Calculation:} \quad \frac{AB \cdot 100}{\Sigma A} = \% \text{ byproduct}$$

AB=peak area of the respective byproduct in the chromatogram of the test solution ΣA=sum of all peak areas in the chromatogram of the test solution except for the injection peak

EXAMPLES 2 TO 7

The experiments in Table 1 were carried out in a similar manner to Example 1

TABLE 1

Various solvent mixtures

| Example | PTC[1] | Solvent | Volume [ml] | Molar equivalents PTC | Yield [% of theory] |
|---|---|---|---|---|---|
| 2 | Dimethylditetra-decylammonium bromide | Toluene | 30 | 0.1 | 48.3 |
| 3 | Dimethylditetra-decylammonium bromide | Toluene | 30 | 0.05 | 53.6 |
| 4 | Dimethylditetra-decylammonium bromide | Diethoxy methane | 25 | 0.1 | 65.4 |
| 5 | Benzyltriethyl ammonium chloride | Diethoxy methane | 30 | 0.05 | 73.7 |
| 6 | Dimethylditetra-decylammonium bromide | Diethoxy methane | 30 | 0.05 | 79.4 |
| 7 | Benzyltriethyl ammonium chloride | Diethoxy methane | 15 | 0.1 | 77.8 |

[1]PTC means phase-transfer catalyst

EXAMPLE 8

2.5 g of 2-cyano-N-(4-trifluoromethylphenyl)acetamide and 15 ml of acetone were charged into a Teflon reactor equipped with a frit. The shaking was turned on and the mixture was cooled to 15° C. 1.73 ml of aqueous 50% strength NaOH were added by hand and 2.12 ml of acetic anhydride were added in the course of 5 to 20 min, with sampling and HPLC monitoring being carried out repeatedly. After the acetic anhydride had been added, the suspension was shaken for a further 8.5 h and cooled to 15° C. In the course of 10 min, 3.20 ml of water and 2.90 ml of HCl, 37%, were each added, with the reactor internal temperature being kept at 5° C. At this temperature, the contents were shaken for 1 h. Subsequently 13.0 ml of water were added, the mixture was warmed to 10° C. and shaken for 1 h. The white suspensions were ejected with argon. The residual solids were washed 3 times, each time with 15.0 ml of deionized water, dried to constant weight at 45° C. and 150 mbar, weighed and analyzed by HPLC.

Yield 2.76 g (92% of theory, HPLC purity 98.3)

EXAMPLE 9

9.1 g of 2-cyano-N-(4-trifluoromethylphenyl)acetamide were weighed into a 200 ml four-neck flask and then suspended adding 49 ml of methyl isobutyl ketone (slightly yellow low-viscosity suspension), which was then cooled to 10° C. At this temperature, 17.8 ml of 33% strength NaOH were added directly from the measuring cylinder. In the course of this the temperature increased to 12° C. and a creamy-colored suspension which was difficult to stir was formed. This was stirred vigorously for 10 min. Thereafter, in the course of 1 h and 20 min, 9.7 ml of acetic anhydride are added dropwise at 7 to 12° C. In the course of this the viscous suspension was converted into a slightly turbid orange solution from which, after 50 min of dropwise addition (about 7 ml added dropwise) a solid crystallized out, as a result of which a spontaneous temperature increase was observed (maximum above 12° C.). After sampling and HPLC analysis, about 1.29% peak area of the starting substance 2-cyano-N-(4-trifluoromethylphenyl)acetamide was still found in the reaction mixture. The dropwise addition was not interrupted. At the end of the dropwise addition after 1 h and 20 min, according to HPLC analysis, complete conversion had been achieved (about 0.13% peak area of 2-cyano-N-(4-trifluoromethylphenyl)acetamide).

The mixture was stirred for a further 50 min, being cooled to 3 to 5° C. Then, at this temperature, 11.5 ml of water were added dropwise in the course of 10 min; the mixture had a pH of 7.1. 16 ml of 37% strength HCl were then added dropwise in the course of 1 h, so that, at a constant temperature, a pH of 1.1 was reached. After further stirring for 25 min, the pH was still 1.1 (creamy-colored non-homogeneous stirrable suspension, as soon as after about 7 ml of HCl). Within the next 20 min, 47.5 ml of water were added dropwise, the temperature increasing to 10° C. The pH increased to 1.7. The mixture was then further stirred for 40 min. Thereafter the suspension was removed by suction and the residue was washed chloride-free 5 times with 30 ml of water. A creamy-colored solid was obtained which was dried under reduced pressure at 40° C.

Yield: 9.8 g (91% of theory, HPLC purity 99.0)

The reactions according to Table 2 were carried out in a similar manner to Examples 8 and 9.

TABLE 2

| Example | Solvent | Equivalents of acetic anhydride | Equivalents of NaOH | Yield [% of theory] | Product (HPLC purity) |
|---|---|---|---|---|---|
| 10 | n-Butanol | 1.5 | 2.25 | 47 | 66.7 |
| 11 | Isopropanol | 1.5 | 2.25 | 63 | 69.3 |
| 12 | Acetone | 1.5 | 2.25 | 92 | 98.3 |
| 13 | Methyl isobutyl ketone | 1.5 | 2.25 | 74 | 93.8 |
| 14 | Methyl isobutyl ketone | 1.5 | 2.26* | 54 | 84.1 |
| 15 | Methyl isobutyl ketone | 2.5 | 5.00** | 91 | 99.0 |
| 16 | N-methyl-pyrrolidone | 1.5 | 2.26 | 58 | 66.5 |

*30% strength NaOH
**33% strength NaOH

What is claimed is:

1. A process for producing the compound of the formula I

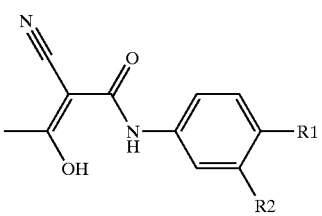

(I)

where
R1 is a) —$CF_3$,
b) —O—$CF_3$,
c) —S—$CF_3$,
d) —OH,
e) —$NO_2$,
f) halogen,
g) benzyl
h) phenyl,
i) —O-phenyl,
k) —CN,
l) —O-phenyl, monosubstituted or polysubstituted with
1) ($C_1$–$C_4$)-alkyl,
2) halogen,
3) —O—$CF_3$ or
4) —O—$CH_3$, and R2 is a) $(C_1-C_4)$-alkyl, b) halogen or c) a hydrogen atom, which comprises reacting a compound of the formula II,

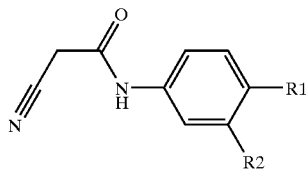

(II)

where R1 and R2 are as defined above, in the presence of at least one base, acetic anhydride and at least one solvent and then isolating the resulting compound of the formula I.

2. The process as claimed in claim 1, wherein a compound of the formula III

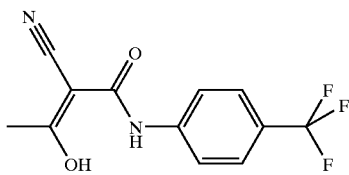

(III)

is prepared from a compound of the formula IV

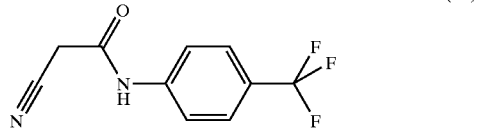

(IV)

and the resulting compound of the formula III is then isolated.

3. The process as claimed in claim 1 or 2, wherein the base used is selected from the group consisting of alkali metal hydroxides, caustic soda, alkali metal hydrides, alkaline earth metal hydrides, amides, alkoxides, organometallic compounds, amines and mixtures thereof.

4. The process as claimed in claim 1 or 2, wherein the solvent used is selected from the group consisting of water; organic solvents selected from the group consisting of ketone solvents, halogenated hydrocarbons, alcohols, ethers, hydrocarbons, esters, aprotic solvents and mixtures thereof; phase-transfer catalysts; crown ethers; cryptands; polyethylene glycols; and mixtures thereof.

5. The process as claimed in claim 1 or 2, wherein the compound of the formula I or III is precipitated out using an acid.

6. The process as claimed in claim 5, wherein the acid is selected from the group consisting of hydrochloric acid, sulfuric acid, nitric acid, phosphoric acid and mixtures thereof.

7. The process as claimed in claim 1 or 2, wherein from 150 mol to 300 mol of acetic anhydride and from 100 mol to 550 mol of sodium hydroxide are used per 100 mol of the compound of the formulae II or IV.

8. The process as claimed in claim 1 or 2, wherein the solvent is used in an amount of from 3 kg to 11 kg, based on 1 kg of the compound of the formula II or IV.

9. The process as claimed in claim 1 or 2, wherein the reaction temperature is from −5° C. to 50° C.

* * * * *